US012761381B2

(12) United States Patent
Jun

(10) Patent No.: US 12,761,381 B2
(45) Date of Patent: Oct. 13, 2026

(54) X-RAY DETECTOR COMPRISING X-RAY SCINTILLATOR

(71) Applicant: DUOPIX-RAY INC., Daejeon (KR)

(72) Inventor: Seung Ik Jun, Frisco, TX (US)

(73) Assignee: DUOPIX-RAY INC., Daejeon (KR)

( * ) Notice: Subject to any disclaimer, the term of this patent is extended or adjusted under 35 U.S.C. 154(b) by 119 days.

(21) Appl. No.: 18/862,044

(22) PCT Filed: Apr. 1, 2024

(86) PCT No.: PCT/KR2024/004132
§ 371 (c)(1),
(2) Date: Oct. 31, 2024

(87) PCT Pub. No.: WO2025/084524
PCT Pub. Date: Apr. 24, 2025

(65) Prior Publication Data

US 2025/0306220 A1 Oct. 2, 2025

(30) Foreign Application Priority Data

Oct. 16, 2023 (KR) ........................ 10-2023-0137700

(51) Int. Cl.
*G01T 1/208* (2006.01)
*A61B 6/42* (2024.01)
*G01T 1/20* (2006.01)
*H10F 39/18* (2025.01)

(52) U.S. Cl.
CPC ............ *G01T 1/208* (2013.01); *A61B 6/4208* (2013.01); *G01T 1/2002* (2013.01); *G01T 1/20184* (2020.05); *H10F 39/1898* (2025.01)

(58) Field of Classification Search
CPC . G01T 1/2018; G01T 1/20184; G01T 1/2002; G01T 1/208; H10F 39/1898
See application file for complete search history.

(56) References Cited

U.S. PATENT DOCUMENTS 5,932,880 A * 8/1999 Koguchi ............... H01J 37/244 250/397
2013/0112882 A1* 5/2013 Osawa ................ G01T 1/20185 250/361 R
2014/0091209 A1* 4/2014 Takei ...................... H10F 77/50 250/216
2023/0184704 A1* 6/2023 Takahashi .......... G01N 23/2251 250/311

FOREIGN PATENT DOCUMENTS

KR 10-2010-0087818 A 8/2010
KR 10-2011-0134227 A 12/2011
KR 10-2012-0030699 A 3/2012
KR 10-2012-0101854 A 9/2012

OTHER PUBLICATIONS

WIPO/ISA/KR, International Search Report issued in International Application No. PCT/KR2024/004132 on Jul. 17, 2024, 3 pages.

* cited by examiner

*Primary Examiner* — Casey Bryant
(74) *Attorney, Agent, or Firm* — J. Peter Paredes; Amin Wasserman Gurnani LLP

(57) ABSTRACT

An X-ray detector is disclosed. The X-ray detector includes: an X-ray detection panel; an X-ray scintillator disposed on the X-ray detection panel; and a conductor disposed adjacent to the X-ray scintillator, wherein the conductor includes at least one of a first conductor disposed between the X-ray detection panel and the X-ray scintillator and a second conductor disposed on the X-ray scintillator.

17 Claims, 5 Drawing Sheets

FIG. 1】
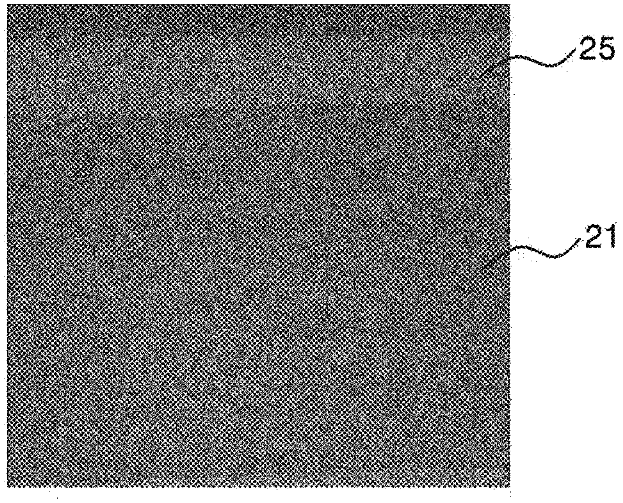
【FIG. 2】
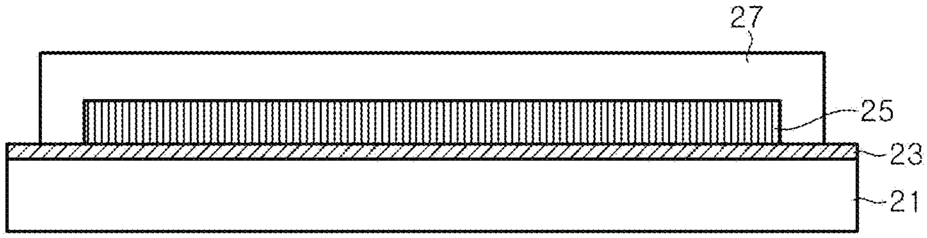
【FIG. 3】
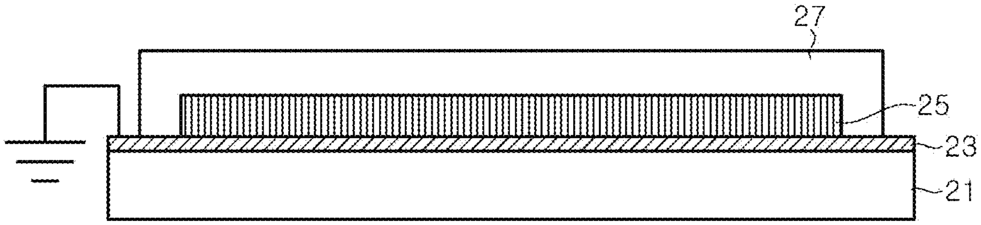

【FIG. 4】
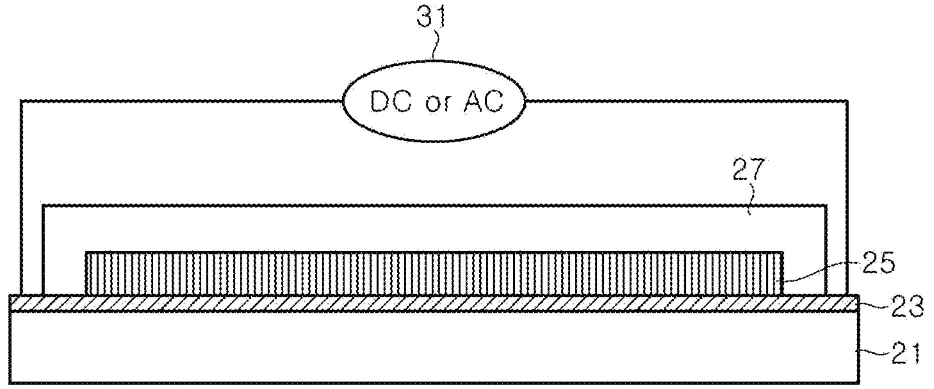
【FIG. 5】
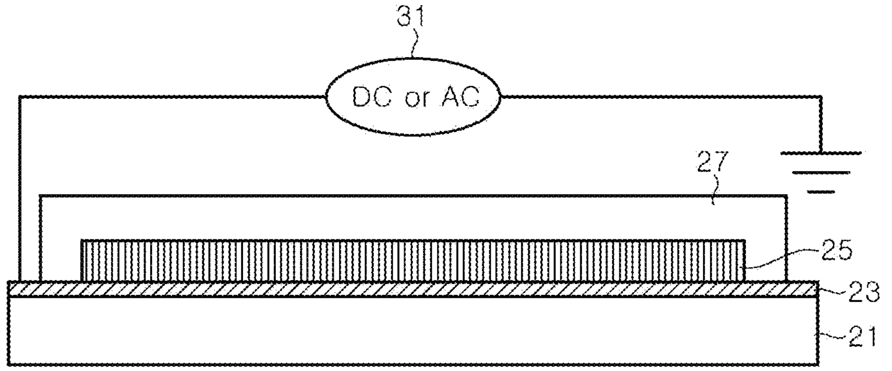
【FIG. 6】
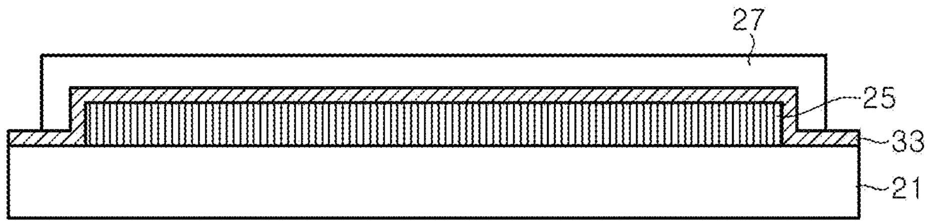

【FIG. 7】
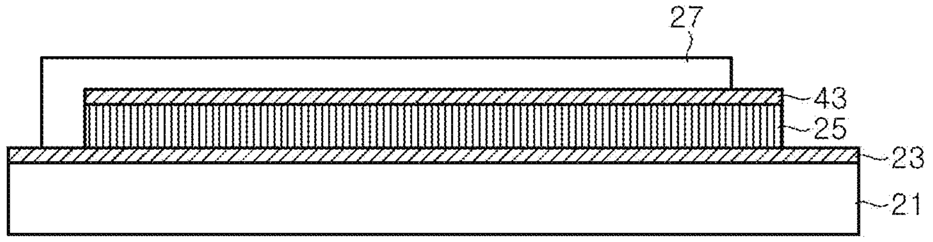
【FIG. 8】
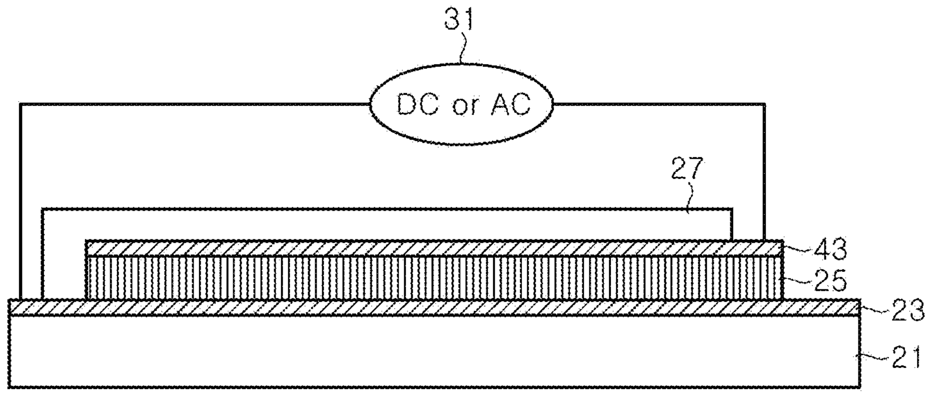
【FIG. 9】
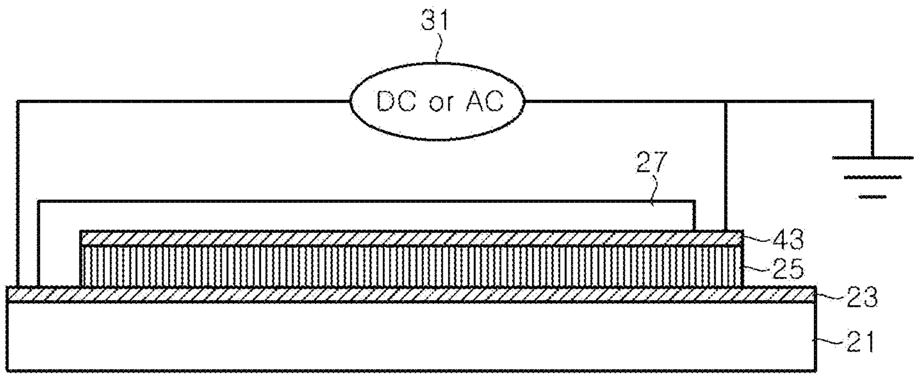

【FIG. 10】
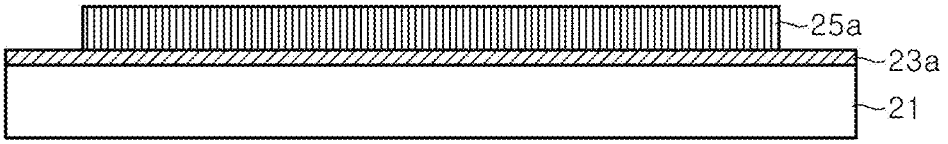
【FIG. 11】
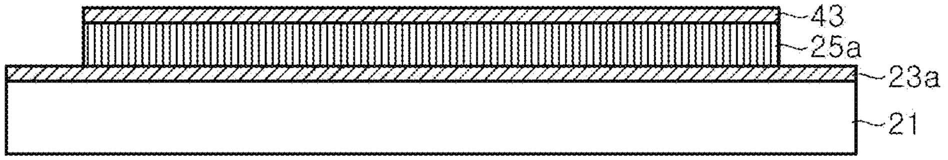
【FIG. 12】
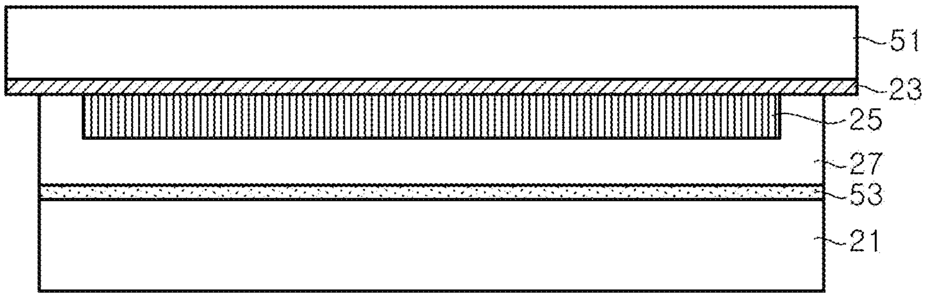

【FIG. 13】
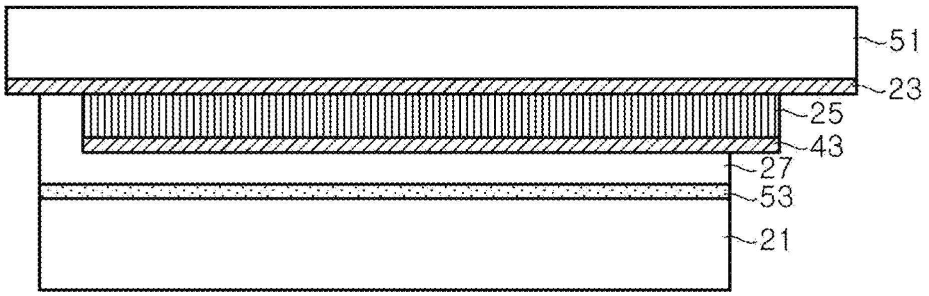

X-RAY DETECTOR COMPRISING X-RAY SCINTILLATOR

TECHNICAL FIELD

The present invention relates to an X-ray detector including an X-ray scintillator and, more particularly, to an X-ray detector capable of rapidly eliminating afterglow of an X-ray scintillator.

BACKGROUND ART

X-ray detectors are used in a wide range of applications, including medical equipment used in hospitals and dental offices for diagnostic X-ray imaging; industrial equipment for inspection of internal defects of electric vehicle batteries, semiconductors, electronic components, buildings, aircrafts, and ships; equipment for security screening of cargo at airports and port facilities; and military equipment for detection of hazardous materials such as explosives.

Dynamic X-ray detectors are used in both medical and industrial applications. In industrial applications, dynamic X-ray detectors play a crucial role in non-destructive testing, which is essential to ensure the safety and reliability of products, such as electric vehicle batteries and semiconductors. In medical applications, dynamic X-ray detectors are used in C-arm CT, cone-beam CT, and breast CT for breast cancer screening.

Such a dynamic X-ray detector requires high frames per second, minimal image lag, and minimal ghost images to achieve high-speed image acquisition.

An X-ray detector includes an X-ray detection panel as an imaging sensor. The X-ray detection panel utilizes a photodiode to detect visible light emitted from a scintillator.

Generally, an X-ray detector includes an X-ray scintillator converting X-rays into visible light and a detection panel detecting visible light generated by the X-ray scintillator. The detection panel includes a photoelectric conversion device, such as a photodiode, and a switching device, such as a thin-film transistor or CMOS.

When X-rays incident on the scintillator have high energy or when the scintillator is irradiated with X rays for a prolonged period of time, afterglow, that is, sustained emission of light from the scintillator, persists for several seconds to tens of seconds after termination of X-ray irradiation before gradually fading over time. The afterglow occurs because it takes a certain amount of time for electrons or ions within the scintillator to become excited and then return to their ground state. FIG. 1 shows afterglow of a scintillator 25 20 seconds after X-ray irradiation in a typical X-ray detector. Even after 20 seconds from the termination of X-ray irradiation, the scintillator 25 disposed on an X-ray detection panel 21 continues to emit light.

Afterglow of the scintillator presents a major obstacle to realization of dynamic X-ray detectors, which require continuous acquisition of sequential X-ray images. Hence, it is imperative to mitigate this phenomenon.

Currently, a method of raising the temperature of an X-ray detector up to 60° C. is used to minimize or rapidly eliminate afterglow of the scintillator. For example, a method of preheating an X-ray detector including a scintillator through continuously operation of the X-ray detector is used. However, this method introduces adverse effects on image quality since temperature-dependent variations in leakage current and threshold voltage occur in internal semiconductor devices as the temperature of the X-ray detector increases. In addition, a preheating time of several minutes to tens of minutes is required to raise the temperature of the X-ray detector, resulting in user inconvenience during imaging examination and diagnosis Therefore, there is a need for an X-ray detector that can rapidly eliminate afterglow of a scintillator without the need to raise the temperature of the X-ray detector.

DISCLOSURE

Technical Problem

It is an aspect of the present invention to provide an X-ray detector that can rapidly eliminate afterglow of a scintillator.

Technical Solution

In accordance with one aspect of the present invention, an X-ray detector is provided. The X-ray detector includes: an X-ray detection panel; an X-ray scintillator disposed on the X-ray detection panel; and a conductor disposed adjacent to the X-ray scintillator. The conductor may include at least one of a first conductor disposed between the X-ray detection panel and the X-ray scintillator or a second conductor disposed on the X-ray scintillator.

In one embodiment, the conductor may adjoin the X-ray scintillator.

In one embodiment, the X-ray scintillator may be formed by vacuum deposition.

In another embodiment, the X-ray scintillator may be formed on the X-ray detection panel by lamination. For example, the X-ray scintillator may be dispersed within a scintillator sheet. In addition, the conductor may include a conductive adhesive.

In one embodiment, the conductor may be in an electrically floating state.

In another embodiment, the conductor may be grounded.

In a further embodiment, the conductor may be connected to an AC or DC power source.

Further, the conductor may include the first conductor and the second conductor, wherein the power source may be electrically connected at one end thereof to the first conductor and may be electrically connected at the other end thereof to the second conductor.

In one embodiment, the power source may be connected at one end or the other end thereof to ground.

The X-ray detector may further include: a protective layer covering the scintillator, wherein the second conductor may be disposed between the scintillator and the protective layer.

The protective layer may be patterned to allow electrical connection to the conductor.

In one embodiment, the X-ray detector may further include: a substrate disposed on the scintillator to be opposite to the X-ray detection panel. The second conductor may be disposed between the scintillator and the substrate.

The X-ray detector may further include: a protective layer disposed between the scintillator and the X-ray detection panel; and a binder disposed between the protective layer and the X-ray detection panel.

The X-ray detector may further include: an AC or DC power source connected to the conductor.

In one embodiment, the conductor may include the first conductor and the second conductor, wherein the power source may be electrically connected at one end thereof to the first conductor and may be electrically connected at the other end thereof to the second conductor.

Further, the power source may be electrically connected at one end or the other end thereof to ground.

Advantageous Effects

Embodiments of the present invention provide an X-ray detector that can rapidly eliminate afterglow of an X-ray scintillator using a conductor disposed adjacent to the X-ray scintillator.

DESCRIPTION OF DRAWINGS

FIG. 1 is a photograph showing afterglow of a scintillator in a typical dynamic X-ray detector.

FIG. 2 is a schematic cross-sectional view of an X-ray detector according to one embodiment of the present invention.

FIG. 3 is a schematic cross-sectional view of an X-ray detector according to another embodiment of the present invention.

FIG. 4 is a schematic cross-sectional view of an X-ray detector according to a further embodiment of the present invention.

FIG. 5 is a schematic cross-sectional view of an X-ray detector according to yet another embodiment of the present invention.

FIG. 6 is a schematic cross-sectional view of an X-ray detector according to yet another embodiment of the present invention.

FIG. 7 is a schematic cross-sectional view of an X-ray detector according to yet another embodiment of the present invention.

FIG. 8 is a schematic cross-sectional view of an X-ray detector according to yet another embodiment of the present invention.

FIG. 9 is a schematic cross-sectional view of an X-ray detector according to yet another embodiment of the present invention.

FIG. 10 is a schematic cross-sectional view of an X-ray detector according to yet another embodiment of the present invention.

FIG. 11 is a schematic cross-sectional view of an X-ray detector according to yet another embodiment of the present invention.

FIG. 12 is a schematic cross-sectional view of an X-ray detector according to yet another embodiment of the present invention.

FIG. 13 is a schematic cross-sectional view of an X-ray detector according to yet another embodiment of the present invention.

BEST MODE

Hereinafter, embodiments of the present invention will be described with reference to the accompanying drawings. It should be understood that the following embodiments are provided for complete disclosure and thorough understanding of the present invention by those skilled in the art. Therefore, the present invention is not limited to the following embodiments and may be embodied in different ways. In the drawings, the width, length, and thickness of components may be exaggerated for descriptive convenience and clarity. When an element is referred to as being "on", "connected to", or "coupled to" another element, it may be directly on, connected to, or coupled to the other element, or intervening elements may be present. It should be noted that like components will be denoted by like reference numerals throughout the specification and the accompanying drawings.

FIG. 2 is a schematic cross-sectional view of an X-ray detector according to one embodiment of the present invention.

Referring to FIG. 2, the X-ray detector includes an X-ray detection panel 21, a scintillator 25, and a conductor 23. The X-ray detector may further include a protective layer.

The scintillator converts incident X-rays into visible light. The X-ray detection panel 21 detects the visible light emitted from the scintillator 25. The X-ray detection panel 21 may include a typical X-ray detection panel 21. The X-ray detection panel 21 includes a plurality of unit pixels (N, N+1, N+2, . . . ), wherein each unit pixel may include a photoelectric conversion device and a switching device. The photoelectric conversion device may include, for example, a photodiode, and the switching device may include, for example, a thin-film transistor or CMOS.

The scintillator 25 emits visible light as electrons excited by incident X-rays return to a ground state. Representative examples of the scintillator 25 may include CsI:TI or GOS, without being limited thereto. It takes a certain amount of time for electrons within the scintillator to become excited by incident X-rays and return to a ground state thereof. In particular, when X-rays incident on the scintillator have high energy or when the scintillator is irradiated with X rays for a prolonged period of time, afterglow, that is, sustained emission of light from the scintillator, can persist for several seconds to tens of seconds after termination of X-ray irradiation.

The conductor 23 is disposed adjacent to the X-ray detection panel 21. As shown in FIG. 2, the conductor 23 may be disposed between the X-ray detection panel 21 and the scintillator 25. Although the conductor 23 may adjoin the scintillator 25, the present invention is not necessarily limited thereto. The conductor 23 may be formed of a transparent conductive oxide layer, a metal layer, or a carbon layer and may consist of a single layer or multiple layers. Examples of the transparent conductive oxide layer may include ITO, ZnO, or SnO, and examples of the metal layer may include Al, AlNd, Mo, W, MoW, or Co.

In this embodiment, the conductor 23 may be formed by vacuum deposition, or may be formed using a conductive film, and the scintillator 25 may be formed by vacuum deposition. In this embodiment, the conductor 23 may be isolated from an external power source and thus may be in an electrically floating state.

The protective layer 27 covers the scintillator 25. The protective layer 27 may cover upper and side surfaces of the scintillator 25. The protective layer 27 may at least partially cover the conductor 23. The protective layer 27 may cover an entirety of the conductor 23, or may cover the conductor 23 while leaving a portion of the conductor 23 exposed, as shown in FIG. 2. The protective layer 27 protects the scintillator 25 from an external environment. The protective layer 27 may be provided as an insulating layer. The protective layer 27 may be formed by vacuum deposition, or may be formed using a protective film.

In this embodiment, the conductor 23 disposed adjacent to the scintillator 25 allows excited electrons in the scintillator 25 to rapidly return to a ground state, thereby enabling rapid elimination of afterglow of the X-ray scintillator.

FIG. 3 is a schematic cross-sectional view of an X-ray detector according to another embodiment of the present invention.

Referring to FIG. 3, the X-ray detector according to this embodiment is substantially the same as the X-ray detector described with reference to FIG. 2 except that a conductor 23 is grounded. In this embodiment, to connect the conductor 23 to ground, the protective layer 27 may be patterned to expose a portion of the conductor 23. By grounding the conductor 23, excited electrons in the scintillator 25 can return to a ground state more rapidly, whereby afterglow of the scintillator afterglow can be eliminated more rapidly.

FIG. 4 is a schematic cross-sectional view of an X-ray detector according to a further embodiment of the present invention.

Referring to FIG. 4, the X-ray detector according to this embodiment is substantially the same as the X-ray detector described with reference to FIG. 2 except that a DC or AC power source 31 is connected to the conductor 23 to apply DC or AC voltage. In this embodiment, to connect the conductor 23 to the power source 31, the protective layer 27 may be patterned to expose the conductor 23. For example, the conductor 23 may be exposed at both ends thereof such that the power source 31 is connected to the exposed ends of the conductor 23. By connecting the power source 31 to the conductor 23, excited electrons in the scintillator 25 can return to a ground state more rapidly, whereby afterglow of the scintillator can be eliminated more rapidly.

FIG. 5 is a schematic cross-sectional view of an X-ray detector according to yet another embodiment of the present invention.

Referring to FIG. 5, the X-ray detector according to this embodiment is substantially the same as the X-ray detector described with reference to FIG. 4 except that a power source 31 is connected at one end thereof to a conductor 23 and is connected at the other end thereof to ground.

FIG. 6 is a schematic cross-sectional view of an X-ray detector according to yet another embodiment of the present invention.

Referring to FIG. 6, the X-ray detector according to this embodiment is substantially the same as the X-ray detector described with reference to FIG. 2 except that a conductor 33 is disposed between a scintillator 25 and a protective layer 27. Although the conductor 33 may adjoin the scintillator 25, the present invention is not necessarily limited thereto.

The conductor 33 may be formed of a transparent conductive oxide layer, a metal layer, or a carbon layer, and may consist of a single layer or multiple layers. Examples of the transparent conductive oxide layer may include ITO, ZnO, or SnO, and examples of the metal layer may include Al, AlNd, Mo, W, MoW, or Co.

In this embodiment, the conductor 33 may be formed by vacuum deposition, or may be formed using a conductive film. In this embodiment, the conductor 33 may be isolated from an external power source and thus may be in an electrically floating state.

Like the conductor 23 of FIG. 2, the conductor 33 may be adjacent to the scintillator 25 to allow excited electrons in the scintillator 25 to rapidly return to a ground state, thereby enabling rapid elimination of afterglow of the X-ray scintillator.

Although the conductor 33 is described as being in an electrically floating state in this embodiment, the present invention is not limited thereto. For example, as described with reference to FIG. 3, the conductor 33 may be connected to ground. Alternatively, as described with reference to FIG. 4, a power source 31 may be connected at both ends to the conductor 33. Alternatively, as described with reference to FIG. 5, the power source 31 may be connected at one end thereof to the conductor 33 and may be connected at the other end thereof to ground.

To connect the conductor 33 to the power source 31 or ground, the protective layer 27 may be patterned to expose at least a portion of the conductor 33.

FIG. 7 is a schematic cross-sectional view of an X-ray detector according to yet another embodiment of the present invention.

Referring to FIG. 7, the X-ray detector according to this embodiment is substantially the same as the X-ray detector described with reference to FIG. 2 except that the X-ray detector further includes a conductor 43.

The conductor 43 may be disposed between a scintillator 25 and a protective layer 27. Although the conductor 43 may adjoin the scintillator 25, the present invention is not necessarily limited thereto. The conductor 43 may be formed of a transparent conductive oxide layer, a metal layer, or a carbon layer, and may consist of a single layer or multiple layers. Examples of the transparent conductive oxide layer may include ITO, ZnO, or SnO, and examples of the metal layer may include Al, AlNd, Mo, W, MoW, or Co. Although the conductor 43 may be formed of the same material as a conductor 23, the present invention is not necessarily limited thereto.

In this embodiment, the conductor 23 and the conductor 43 may be in an electrically floating state, or may be connected to ground. Although the conductor 43 may be electrically isolated from the conductor 23, the present invention is not limited thereto. That is, the conductor 43 may adjoin the conductor 23, or the upper, lower, and side surfaces of the scintillator 25 may be covered by the conductor 23 and the conductor 43.

A protective layer 27 covers the conductor 43. Although the protective layer 27 may cover an entirety of the conductor 43, the protective layer 27 may cover the conductor 43 while leaving a portion of the conductor 43 exposed, as shown in FIG. 7.

By disposing the conductors 23, 43 to cover a large surface area of the scintillator 25, afterglow of the scintillator can be more rapidly eliminated.

FIG. 8 is a schematic cross-sectional view of an X-ray detector according to yet another embodiment of the present invention.

Referring to FIG. 8, the X-ray detector according to this embodiment is substantially the same as the X-ray detector described with reference to FIG. 7 except that a DC or AC power source 31 is connected to conductors 23, 43. The power source 31 may be connected at one end thereof to the conductor 23 and may be connected at the other end thereof to the conductor 43.

To connect the power source 31 to the conductors 23, 43, a protective layer 27 may be patterned to expose a portion of each of the conductors 23, 43.

FIG. 9 is a schematic cross-sectional view of an X-ray detector according to yet another embodiment of the present invention.

Referring to FIG. 9, the X-ray detector according to this embodiment is substantially the same as the X-ray detector described with reference to FIG. 8 except that the other end of the power source 31 is connected to ground. Alternatively, the one end of the power source 31 may be connected to ground.

FIG. 10 is a schematic cross-sectional view of an X-ray detector according to yet another embodiment of the present invention.

Referring to FIG. 10, the X-ray detector according to this embodiment is the same as the X-ray detector described with reference to FIG. 2 except that, instead of the scintillator 25 formed by vacuum deposition, a scintillator sheet 25*a* is attached to an X-ray detection panel 21 by lamination. The scintillator sheet 25*a* may be attached to the X-ray detection panel 21 using a conductive adhesive 23*a*. The conductive adhesive 23*a* may be formed using a conductive adhesive paste or a conductive tape.

The scintillator sheet 25*a* includes a matrix and scintillator particles dispersed within the matrix. Since the scintillator particles are dispersed within the matrix, a protective layer 27 for protection of the scintillator particles may be omitted.

In this embodiment, the conductive adhesive 23*a* performs the same function as the conductor 23 described in FIG. 2 and thus allows rapid elimination of afterglow of the scintillator particles in the scintillator sheet 25*a*.

The conductive adhesive 23*a* may be in an electrically floating state, as described with reference to FIG. 2, may be grounded, as described with reference to FIG. 3, or may be connected to a power source 31, as described with reference to FIG. 4 and FIG. 5.

FIG. 11 is a schematic cross-sectional view of an X-ray detector according to yet another embodiment of the present invention.

Referring to FIG. 11, the X-ray detector according to this embodiment is substantially the same as the X-ray detector described with reference to FIG. 10 except that the X-ray detector further includes a conductor 43 on a scintillator sheet 25*a*. Since the conductor 43 is the same as described with reference to FIG. 7, detailed description thereof will be omitted to avoid redundancy.

As described with reference to FIG. 8 and FIG. 9, a conductive adhesive 23*a* and the conductor 43 may be connected to a power source 31.

FIG. 12 is a schematic cross-sectional view of an X-ray detector according to yet another embodiment of the present invention.

Referring to FIG. 12, the X-ray detector according to this embodiment includes an X-ray detection panel 21, a conductor 23, a scintillator 25, a protective layer 27, a substrate 51, and a binder 53.

Since the X-ray detection panel 21, the conductor 23, the scintillator 25, and the protective layer 27 are the same as described with reference to FIG. 2 except for a stacking structure thereof, the following description will focus on differences from the embodiment of FIG. 2.

The substrate 51 may be any substrate that can transmit X-rays, without particular restriction. The conductor 23 is disposed between the substrate 51 and the scintillator 25. The conductor 23 is disposed adjacent to the scintillator 25. In one embodiment, the conductor 23 may adjoin the scintillator 25.

The protective layer 27 covers the scintillator 25. The protective layer 27 may be patterned to expose the conductor 23.

The binder 53 is disposed between the X-ray detection panel 21 and the protective layer 27 to bond the X-ray detection panel 21 to the protective layer 27.

In this embodiment, the scintillator 25 is formed on the substrate 51 by vacuum deposition. The conductor 23 may be formed on the substrate 51 prior to forming the scintillator 25. The protective layer 27 may be formed after formation of the scintillator 25. Thereafter, the substrate 51 with the scintillator 25 formed thereon is bonded to the X-ray detection panel 21 by the binder 53. For example, the substrate 51 may be bonded to the X-ray detection panel 21 by the binder 53 with the protective layer 27 facing the X-ray detection panel 21.

Although the conductor 23 is described as being disposed between the substrate 51 and the scintillator 25 in this embodiment, the present invention is not limited thereto and the conductor 23 may be disposed between the scintillator 25 and the protective layer 27, like the conductor 33 described with reference to FIG. 6.

Although the conductor 23 may be in an electrically floating state, the present invention is not limited thereto and the conductor 23 may be grounded or may be connected to a power source 31, as described with reference to FIG. 3, FIG. 4, or FIG. 5.

FIG. 13 is a schematic cross-sectional view of an X-ray detector according to yet another embodiment of the present invention.

Referring to FIG. 13, the X-ray detector according to this embodiment is the same as the X-ray detector described with reference to FIG. 12 except that the X-ray detector further includes a conductor 43. Since the conductor 43 is the same as the conductor 43 described with reference to FIG. 7, detailed description thereof will be omitted.

In this embodiment, the conductors 23, 43 may be in an electrically floating state, as described with reference to FIG. 7, may be grounded, or may be connected to a power source 31, as described with reference to FIG. 8 and FIG. 9.

Although some embodiments have been described, it should be understood that these embodiments are provided for illustration only and are not to be construed in any way as limiting the present invention, and that various modifications, changes, alterations, and equivalent embodiments can be made by those skilled in the art without departing from the spirit and scope of the invention.

The invention claimed is:

1. An X-ray detector comprising:

an X-ray detection panel;

an X-ray scintillator disposed on the X-ray detection panel; and a conductor disposed adjacent to the X-ray scintillator, wherein the conductor comprises at least one of a first conductor disposed between the X-ray detection panel and the X-ray scintillator and a second conductor disposed on the X-ray scintillator.

2. The X-ray detector according to claim 1, wherein the conductor adjoins the X-ray scintillator.

3. The X-ray detector according to claim 1, wherein the X-ray scintillator is disposed in direct contact with X-ray detection panel.

4. The X-ray detector according to claim 1, wherein the X-ray scintillator is dispersed within a scintillator sheet.

5. The X-ray detector according to claim 4, wherein the conductor comprises a conductive adhesive.

6. The X-ray detector according to claim 1, wherein the conductor is in an electrically floating state.

7. The X-ray detector according to claim 1, wherein the conductor is grounded.

8. The X-ray detector according to claim 1, wherein the conductor is connected to an AC or DC power source.

9. The X-ray detector according to claim 8, wherein the conductor comprises the first conductor and the second conductor, and the power source is electrically connected at one end thereof to the first conductor and is electrically connected at the other end thereof to the second conductor.

10. The X-ray detector according to claim 9, wherein the power source is connected at one end or the other end thereof to ground.

11. The X-ray detector according to claim 1, further comprising:

a protective layer covering the scintillator, wherein the second conductor is disposed between the scintillator and the protective layer.

12. The X-ray detector according to claim 11, wherein the protective layer is patterned to allow electrical connection to the conductor.

13. The X-ray detector according to claim 1, further comprising:

a substrate disposed on the scintillator to be opposite to the X-ray detection panel, wherein the second conductor is disposed between the scintillator and the substrate.

14. The X-ray detector according to claim 13, further comprising:

a protective layer disposed between the scintillator and the X-ray detection panel; and a binder disposed between the protective layer and the X-ray detection panel.

15. The X-ray detector according to claim 14, further comprising:

an AC or DC power source connected to the conductor.

16. The X-ray detector according to claim 15, wherein the conductor comprises the first conductor and the second conductor, and the power source is electrically connected at one end thereof to the first conductor and is electrically connected at the other end thereof to the second conductor.

17. The X-ray detector according to claim 15, wherein the power source is electrically connected at one end or the other end thereof to ground.

* * * * *